(12) United States Patent
Murray et al.

(10) Patent No.: US 11,235,130 B2
(45) Date of Patent: Feb. 1, 2022

(54) CATHETER WITH RING-SHAPED DRAINAGE MEMBER

(71) Applicant: Hollister Incorporated, Libertyville, IL (US)

(72) Inventors: Michael G. Murray, Ballina (IE); Robert Miculas, Baia Mare (RO); Michelle Murphy, Dublin (IE); Patrick Enda O'Dowd, Dunsany (IE)

(73) Assignee: Hollister Incorporated, Libertyville, IL (US)

( * ) Notice: Subject to any disclaimer, the term of this patent is extended or adjusted under 35 U.S.C. 154(b) by 142 days.

(21) Appl. No.: 16/485,515

(22) PCT Filed: Feb. 12, 2018

(86) PCT No.: PCT/US2018/017818
§ 371 (c)(1),
(2) Date: Aug. 13, 2019

(87) PCT Pub. No.: WO2018/148658
PCT Pub. Date: Aug. 16, 2018

(65) Prior Publication Data
US 2020/0016380 A1 Jan. 16, 2020

Related U.S. Application Data

(60) Provisional application No. 62/458,334, filed on Feb. 13, 2017.

(51) Int. Cl.
*A61M 27/00* (2006.01)
*A61M 25/00* (2006.01)
*A61M 25/01* (2006.01)

(52) U.S. Cl.
CPC ........ *A61M 27/00* (2013.01); *A61M 25/0097* (2013.01); *A61M 25/0136* (2013.01);
(Continued)

(58) Field of Classification Search
CPC .............. A61M 25/00; A61M 25/0017; A61M 25/0136; A61M 39/10; A61M 25/0043;
(Continued)

(56) References Cited

U.S. PATENT DOCUMENTS 5,653,700 A 8/1997 Byrne et al.
6,447,523 B1 9/2002 Middleman et al.
(Continued)

FOREIGN PATENT DOCUMENTS

WO WO 2005/014097 A1 2/2005
WO WO 2014/062225 A1 4/2014
(Continued)

OTHER PUBLICATIONS

International Search Report and Written Opinion of the International Searching Authority dated Jun. 25, 2018 for International Application No. PCT/US2018/017818.

*Primary Examiner* — Andrew J Mensh
*Assistant Examiner* — Nhu Q. Tran
(74) *Attorney, Agent, or Firm* — Cook Alex Ltd.

(57) ABSTRACT

A catheter (24) and catheter assembly (22) having a drainage member (46), defining a generally ring-shaped opening (48).

17 Claims, 5 Drawing Sheets

(52) U.S. Cl.
CPC ............... *A61M 2202/0496* (2013.01); *A61M 2205/586* (2013.01); *A61M 2210/1089* (2013.01)

(58) Field of Classification Search
CPC ........ A61M 2210/1089; A61B 17/3417; A61F 2005/4402
USPC .......................................................... 604/544
See application file for complete search history.

(56) References Cited

U.S. PATENT DOCUMENTS

| | | | |
|---|---|---|---|
| 6,485,438 B1 | 11/2002 | Minue | |
| 7,135,010 B2 | 11/2006 | Buckman et al. | |
| 7,789,873 B2 | 9/2010 | Kubalak et al. | |
| 8,827,984 B2 | 9/2014 | Lovmar et al. | |
| 8,919,553 B2 | 12/2014 | Murray et al. | |
| 8,920,363 B2 | 12/2014 | Patterson et al. | |
| 8,932,262 B2 | 1/2015 | Ostfeld et al. | |
| 9,480,821 B2 * | 11/2016 | Ciccone | A61M 25/0017 |
| 2013/0161227 A1 | 6/2013 | Gustavsson | |
| 2014/0221984 A1 | 8/2014 | Triel et al. | |
| 2015/0018803 A1 * | 1/2015 | Tjassens | A61M 25/002 604/544 |
| 2015/0273183 A1 | 10/2015 | Foley et al. | |
| 2016/0001037 A1 * | 1/2016 | Hong | A61M 25/0111 604/544 |
| 2016/0193447 A1 | 7/2016 | Matthiassen | |
| 2016/0228679 A1 | 8/2016 | Foley et al. | |
| 2018/0021481 A1 * | 1/2018 | Yin | A61M 25/0045 206/364 |
| 2018/0071486 A1 * | 3/2018 | O'Flynn | A61M 25/0662 |

FOREIGN PATENT DOCUMENTS

| | | |
|---|---|---|
| WO | WO 2014/142923 A1 | 9/2014 |
| WO | WO 2015/089165 A2 | 6/2015 |

* cited by examiner

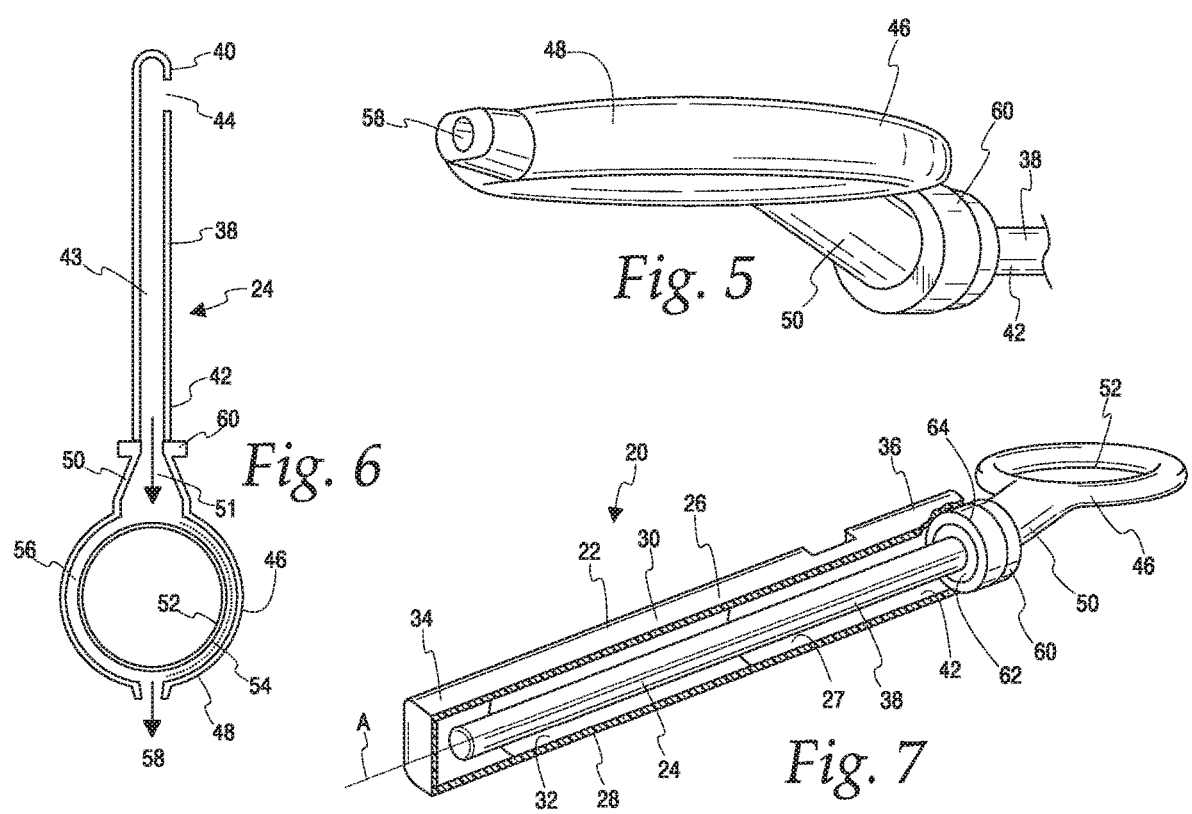

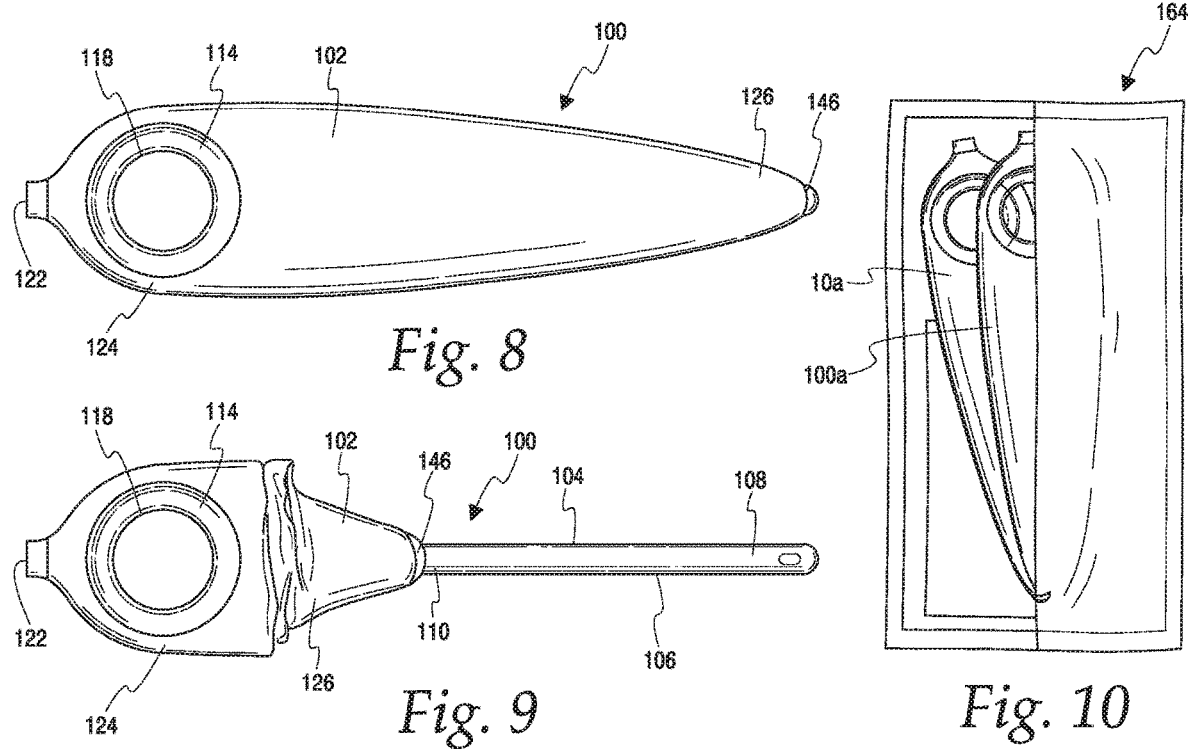

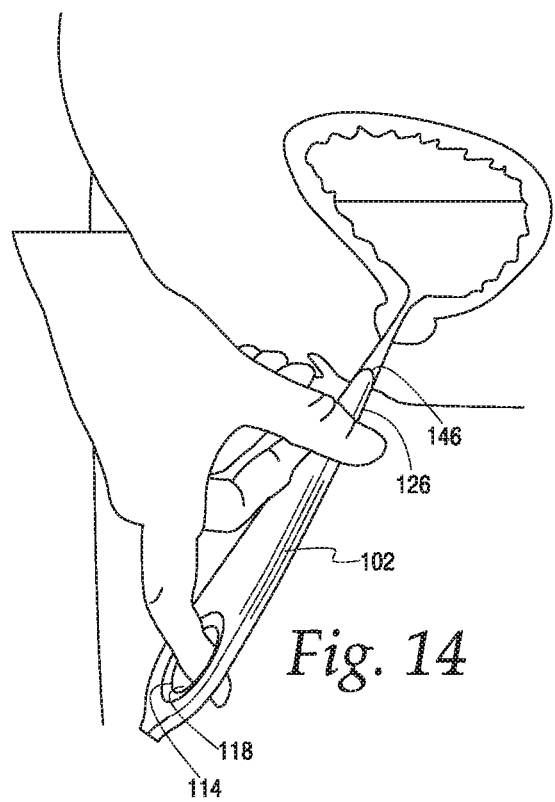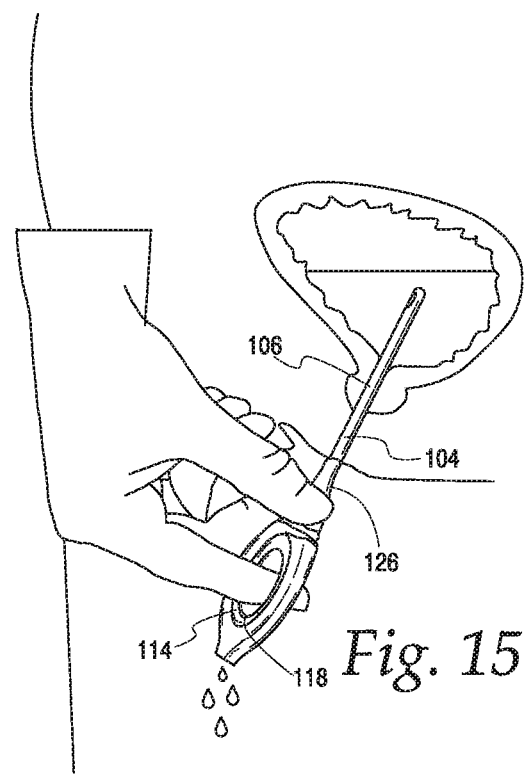

CATHETER WITH RING-SHAPED DRAINAGE MEMBER

RELATED APPLICATION

The present application is the U.S. National Stage Application of PCT Application No. PCT/US2018/017818, filed Feb. 12, 2018, which claims the benefit and priority of U.S. Provisional Patent Application No. 62/458,334, filed Feb. 13, 2017, both of which are hereby incorporated herein by reference.

TECHNICAL FIELD

The present disclosure is directed to catheters for use in the medical field. More particularly, the present disclosure is directed to urinary catheters for use in the management of urinary incontinence. Even more particularly, the present disclosure is directed to compact intermittent urinary catheters.

BACKGROUND

Catheters are used to treat many different types of medical conditions and typically include an elongated catheter tube that is inserted into and through a passageway or lumen of the body. Urinary catheters and, in particular, intermittent urinary catheters are commonly used by individuals who suffer from certain abnormalities of the urinary system, such as urinary incontinence. With the advent of intermittent urinary catheters, individuals with problems associated with the urinary system can conveniently self-catheterize to drain the individual's bladder. Individuals who suffer from urinary incontinence will self-catheterize several times a day.

Self-catheterization involves removing the catheter assembly from its package and inserting and advancing the catheter tube through the urethra. Users of intermittent catheters are often required to self-catheterize outside the privacy of the home, such as in public restrooms. Thus, for these and other reasons, it is desirable for the intermittent catheters to be easy to handle, especially for users with limited dexterity. It is also desirable that the catheters are provided in discrete packaging that is easy to open, compact and portable, and easy to dispose.

SUMMARY

In one aspect, a urinary catheter includes a catheter tube having a proximal insertion end portion, a distal end portion and a lumen. The catheter also includes a drainage member associated with the distal end portion of the catheter tube wherein the drainage member defines one or more generally ring-shaped openings and has at least one drainage passageway in fluid communication with the lumen of the catheter tube.

In another aspect, a urinary catheter assembly including a case that has a cavity. The assembly also includes a urinary catheter that includes a catheter tube having a proximal insertion end portion, a distal end portion and a lumen. The catheter also includes a drainage member associated with the distal end portion of the catheter tube wherein the drainage member defines a generally ring-shaped opening and has at least one drainage passage in fluid communication with the lumen of the catheter tube. At least the catheter tube being located within the cavity of the case.

BRIEF DESCRIPTION OF THE DRAWINGS

FIG. 5 is a partial perspective of the catheter shown in FIG. 4.

FIG. 6 is a schematic view of the catheter shown in FIG. 4.

FIG. 7 is a cross-sectional view of the catheter assembly shown in FIG. 1.

FIG. 8 is a front plan view of another embodiment of a catheter assembly of the present disclosure.

FIG. 9 is a perspective view of the catheter assembly of FIG. 8 shown with the case in a collapsed configuration.

FIG. 10 is a cutaway plan view of a package containing multiple catheter assemblies.

FIGS. 14 and 15 are schematic views illustrating the use of the catheter assembly of FIG. 8.

DESCRIPTION

Figure 1:
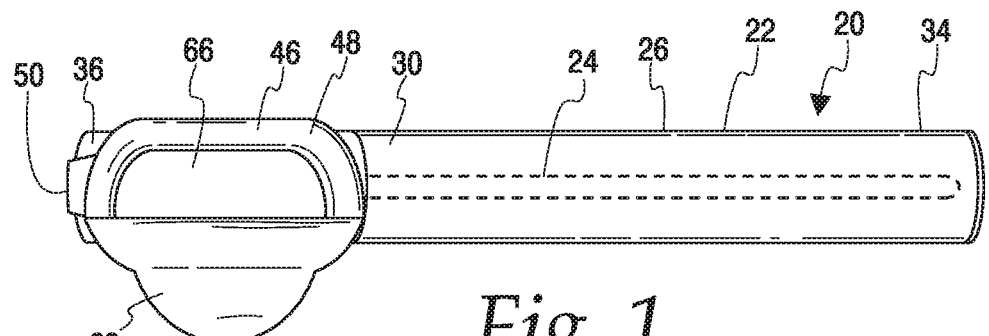
FIG. 1 is a front plan view of one embodiment of a catheter assembly of the present disclosure.

While the subject matter of the present disclosure will be described in terms of certain preferred or alternative embodiments, it is contemplated that the present subject matter may employ various structures, modifications and alternatives.

FIGS. 1-3 and 7 illustrate a catheter assembly 20 in accordance with the present disclosure. Catheter assembly 20 includes a case 22 and a urinary catheter 24. Case 20 may be a hollow tube 26 having a lumen 27 defined by a wall 28 having an outer surface 30 and an inner surface 32 (shown in FIG. 7). Hollow tube 26 includes a closed proximal end 34 and an opening at the distal end 36 for receiving at least a portion of the urinary catheter 24 into the lumen 27 of tube 26. The outer profile the tube 26 and cross-sectional shape of the lumen 27 defined by wall 28 may be substantially the same or different. Additionally, the outer profile of the tube 26 and cross-sectional shape of the lumen 27 may be any variety of shapes, including but not limited to, generally circular, triangular, rectangular, oval, elliptical, pentagonal, hexagonal, etc.

Referring to FIGS. 3-7, urinary catheter 24 includes a catheter tube 38 having a proximal insertion end portion 40, a distal end portion 42, and a lumen 43 (FIG. 6). The proximal insertion end portion 40 includes at least one drainage opening, such as eyelet 44, for draining urine from the bladder into lumen 43. A drainage member 46 is associated with the distal end portion 42 of the catheter tube 38. Drainage member 46 has a generally ring-shaped opening 52 extending therethrough, which may be configured to receive the finger of a user during use. In an alternative embodiment, the drainage member may have more than one ring-shaped opening 52. The one or more ring-shaped openings may be ergonomically shaped and sized for convenient grasping and manipulation of the urinary catheter during a catheterization procedure. In the illustrated embodiment, the drainage member 46 includes a generally ring-shaped portion 48 that defines the generally ring-shaped opening 52. Optionally, the drainage member 46 may include a stem 50 extending from the ring-shaped portion 48. Although the ring-shaped portion 48 and opening 52 are shown as generally circular, they may be any variety of shapes, including but not limited to triangular, rectangular, oval, elliptical, pentagonal, hexagonal, etc. The drainage member 46 and ring-shaped portion 48 may be made from material(s) that allows the drainage member to be bent or deformed for directing the drainage of urine or for packaging of the catheter assembly, as will be explained in more detail below. In one embodiment, the drainage member may be made from a resilient material. The material may include but is not limited to Thermoplastics, Thermoplastic Elastomers (TPE), Polyurethane, Polyethylene, Polypropylene, Silicon, Rubber, Copolymers, Polyether, Polyamide and Polyester.

Referring to FIG. 6, the ring-shaped portion 48 may include at least one drainage passageway 54 extending along one side of the ring-shaped opening 52 and in fluid communication with the lumen 43 of catheter tube 38. The ring-shaped portion 48 may, optionally, include a second drainage passageway 56 extending along the other side of the ring-shaped opening 52. The ring-shaped portion 48 also includes a drainage opening 58 for the passage of urine out of the catheter 24. The drainage opening 58 can be configured to direct urine directly into a toilet or can be configured to be connected to a urine collection bag.

The stem 50, when one is present, includes a fluid passageway 51 and is connected to the distal end portion 42 of the catheter tube 38. Referring to FIG. 7, the stem 50 may include a hub 60 that connects the drainage member 46 to the distal end portion 42 of the catheter tube 38. The hub 60 may include an inner core 62 surrounding and attached to the distal end portion 42 of the catheter tube 38 and an outer layer 64 which is connected to or integral with the stem 50. The inner core 62 may be for example polypropylene. Furthermore, as shown in FIGS. 5 and 7, the stem 50 may extend at angle from one or both of the ring-shaped portion 48 and the catheter tube 38 such that the drainage opening 58 is offset from the elongated axis A (FIG. 7) of the lumen 43 of the catheter tube 38. This may aid the user in handling and directing urine from the catheter and make it less likely for the user to get urine on their hands. In another embodiment, the drainage opening 58 may be coaxial with the axis A of the catheter tube.

The case 22 and the catheter 24 may engage each other in a sealing relationship so that the hollow tube 26 of the case, having the catheter therein, is sealed from the outer atmosphere to keep the insertable portion of the catheter 24 in a sterile condition. For example, the drainage member 46 may form a seal with the opening at the distal end 36 of the case 22. Referring to FIG. 7, in the illustrated embodiment, the hub 60 of the catheter 24 may form a seal with the inner wall 32 of the hollow tube 26 to seal the lumen 27 of tube 26 from the atmosphere. The seal is a breakable seal that may be, for example, a friction fit, an adhesive seal, a heat seal, weld, etc.

The catheter 24 may be of the type that is lubricated with a gel (gel-lubricated) or of the type that has a lubricous hydrophilic coating. When the catheter 24 is a gel-lubricated catheter, the user may apply gel to the catheter after the catheter has been removed from the case 22. In another embodiment, the case 22 may include a cartridge that contains a gel and applies it to the catheter tube 38. For example, the case 22 may include a ring-shaped cartridge that surrounds the catheter tube 38. As the catheter tube 38 is removed from the case 24 it passes through the ring-shaped cartridge, which applies a gel as the catheter tube 38 passes therethrough. When the catheter tube 38 has a lubricous hydrophilic coating, the case 22 may include a hydrating agent, such as aqueous solution, liquid water or water vapor. The hydrating agent may be a liquid in direct contact or indirect contact with the lubricous hydrophilic coating to hydrate the coating. In another embodiment, the hydrating agent may be a liquid that is contained in a gas permeable, liquid impermeable compartment, so that liquid is separated from the hydrophilic coating. The liquid in the compartment provides a vapor that permeates through the gas permeable, liquid impermeable compartment wherein the vapor hydrates the hydrophilic coating. The gas permeable, liquid impermeable compartment may be an elongated sachet that is placed in the lumen 27 of hollow tube 26. The sachet may be free within the tube 26 or may be attached to inner surface 32.

Referring back to FIG. 1, this figure shows the catheter assembly 20 in a packaged, pre-use configuration. In the packaged configuration, the catheter 24 is located in the hollow tube 26 of case 22 with the drainage member 46 extending from the opening of the case and bent over the distal end portion 36 of the case 22 and secured to the outer wall 30 of the case. In the illustrated embodiment, the ring-shaped opening 52 of the ring-shaped portion 48 of the drainage member 46 receives a boss 66 on the outer wall 30 of the case. The boss 66 has a generally elongated shape. The ring-shaped portion 48 is deformed so as to accommodate the elongated boss 66, resulting in a friction fit that hold the ring-shaped portion 48 in place. In addition to the boss 66, or as an alternative, the catheter assembly 20 may also include an adhesive element 68 that is positioned over the ring-shaped portion 48 to hold it in place. The adhesive element 68 may be an adhesive tab that could also serve as a security seal. When the stem 50 of the drainage member 46 is bent as shown in FIG. 1, it is pinched down to close of the fluid passageway 51 therein and close the lumen of the catheter 24 from the outer atmosphere. In addition to or alternatively, the adhesive element 68 could include a portion that covers the drainage opening 58 to close the lumen of the catheter 24 from the outer atmosphere.

Figure 2:
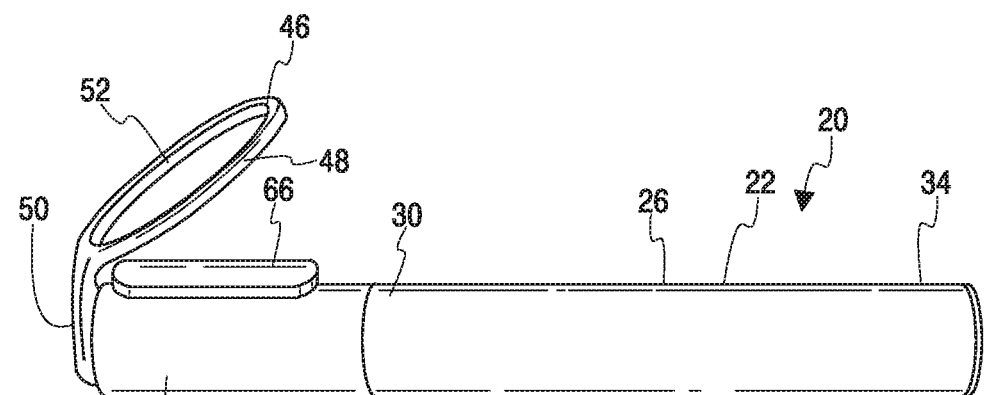
FIG. 2 is a side perspective view of the catheter assembly of FIG. 1.
Figure 3:
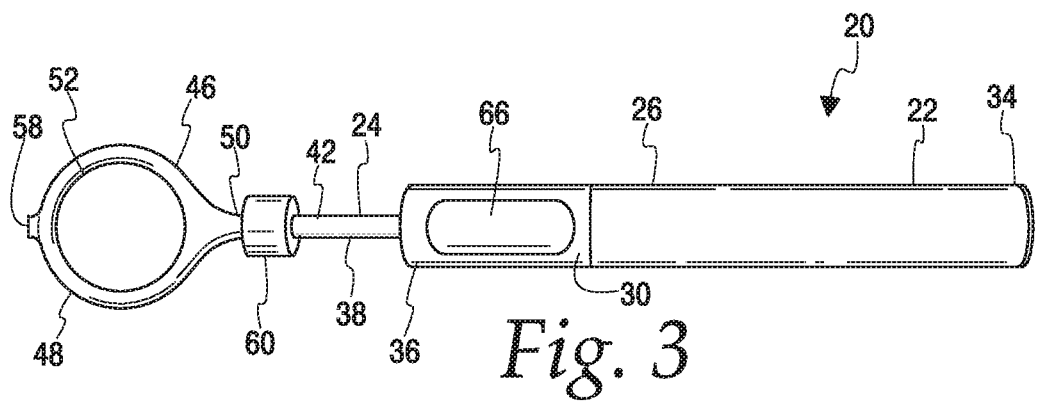
FIG. 3 is a front perspective view of the catheter assembly of FIG. 1 shown with the catheter being partially removed from the case.
Figure 4:
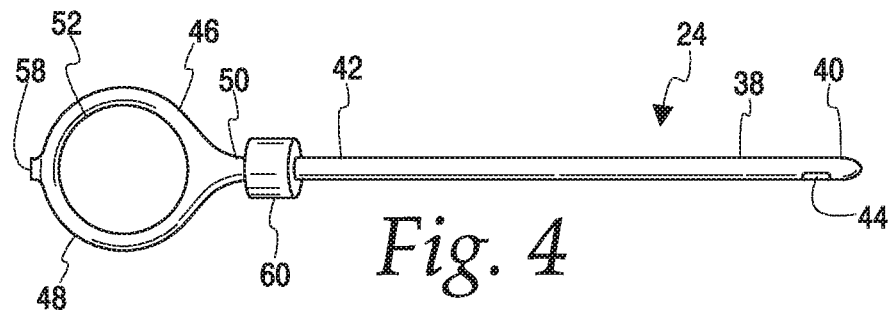
FIG. 4 is a side perspective view of the catheter shown FIG. 1.
Figure 11:
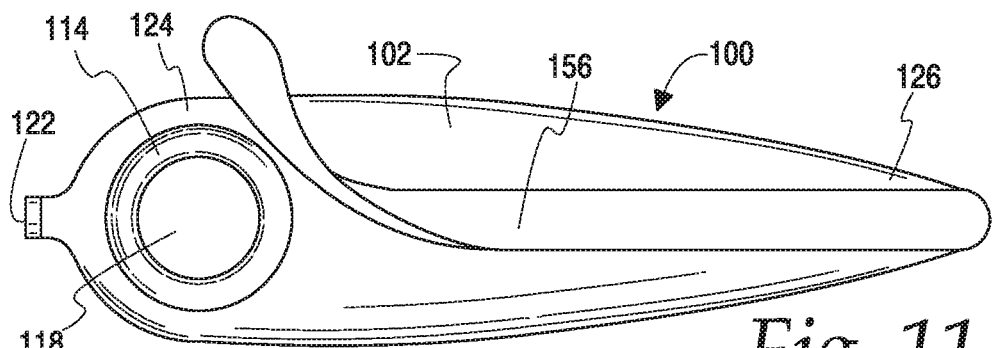
FIG. 11 is a perspective view of the catheter assembly of FIG. 8 shown with a sealing element.

Referring to FIGS. 1-3, when the user is ready to use the catheter assembly 20, the user peels off the adhesive element 68, if one is present, (FIG. 1) and then detaches the ring-shaped portion 48 of the drainage member 46 from the boss 66. When the drainage member 46 is made of a resilient material, the ring-shaped member 48 will move into the position shown in FIG. 7. Referring to FIG. 3, the user then grasps the drainage member 46 and pulls the catheter 24 out of the case 22. When doing so, the user has the option of inserting a finger through opening 52 in the ring-shaped portion 48, which may be especially beneficial to users with limited dexterity.

Once removed from the case 22, the insertable proximal portion 40 of the catheter tube 38 is inserted into the urethra to access the bladder. Once the eyelets 44 are inserted into the bladder, urine enters the eyelets 44 and flows through the lumen 43 of the catheter tube 38 toward drainage member 46. The urine flows through one or both drainage passageways 54, 56 and out of the drainage opening 58. The user may bend the drainage member 46, as needed, to aim the drainage of urine.

Figure 12:
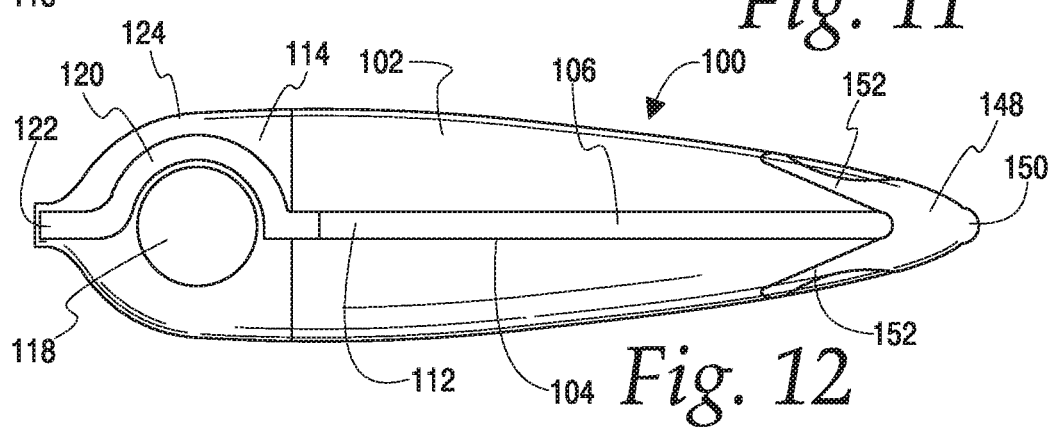
FIG. 12 is a schematic view of the catheter assembly of FIG. 8 showing one embodiment of a fluid path and an insertion element within the case.
Figure 13:
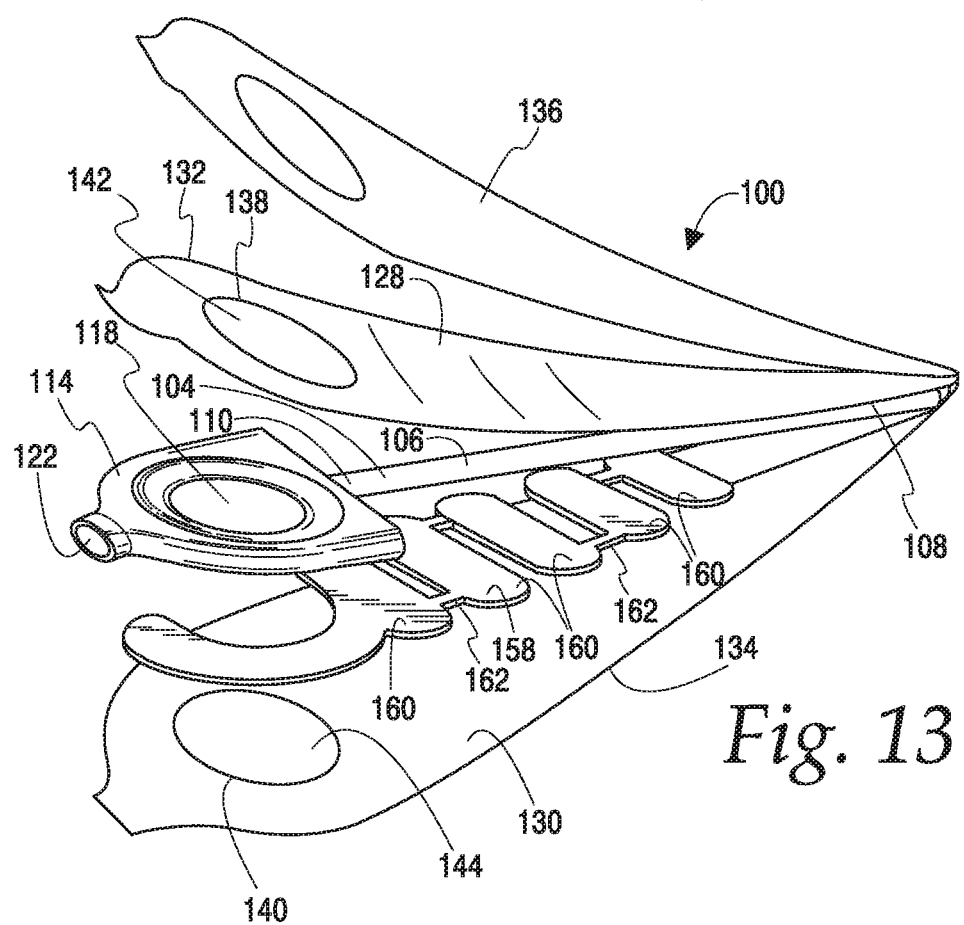
FIG. 13 is an exploded view of one embodiment of the catheter assembly of FIG. 8.

FIGS. 8-15 illustrate another embodiment of a catheter assembly 100 of the present disclosure. Referring to FIGS. 8, 9 and 12, the catheter assembly 100 includes a case 102 and a catheter 104. Referring to FIGS. 9, 12 and 13, the catheter 104 includes a catheter tube 106 having a proximal end portion 108, a distal end portion 110 and a lumen 112 (FIG. 12). The catheter 104 also includes a drainage member 114 associated with the distal end portion 110 of the catheter tube 106. The drainage member 114 defines a generally ring-shaped opening 118 extending therethrough, which may be configured to receive a user's finger. Although the ring-shaped opening 118 is shown as generally circular, it may be any variety of shapes, including but not limited to triangular, rectangular, oval, elliptical, pentagonal, hexagonal, etc. The drainage member 114 may also be any variety of shapes. For example, the illustrated drainage member 114 has a generally squarish proximal end and a generally rounded distal end. The drainage member 114 may also be any of the above-mentioned shapes.

Referring to FIG. 12, the drainage member 114 may include at least one fluid passageway 120 extending along one side of the ring-shaped opening 118. It may also include a second fluid passageway (not shown) extending along the other side of the ring-shaped opening 118, similar to that shown above in FIG. 6. The drainage member 114 also includes a drainage opening 122 for drainage of urine from the catheter assembly 100.

The case 102 may be a collapsible case that surrounds the catheter 104. In the illustrated embodiment, the case 102 has a generally leaf-like shape wherein the case 102 is wider at the distal end portion 124 and tapers in width toward the proximal end portion 126. The case could have other configurations and shapes as well. The collapsible case 102 is made from a flexible material that is foldable or collapsible. For example, the case 102 may be made from a polymer film or a laminate that includes a layer(s) of polymer film and a layer(s) of metal, such as aluminum. In one embodiment, the case 102 may be made from a liquid and gas impermeable material, such as a laminate of polymer and aluminum.

Referring to FIGS. 12 and 13, the case 102 surrounds the catheter tube 106 of catheter 104. The case 102 may also cover or at least partially cover the drainage member 114. Referring to FIG. 13, in one embodiment, the case 102 includes a front panel 128 and a rear panel 130 that are sealed together along their respective peripheral edges 132 and 134. The case 102 may optionally include a decorative panel 136 that is sealed to the front panel 128 and provides aesthetically pleasing artwork, designs or textures. The front and back panels 128 and 130 may each include a respective inner edge 138, 140 that defines an opening 142, 144 that is generally the same shape as the ring-shaped opening 118 of the drainage member 114. The inner edges 138, 140 may be attached to the drainage member 114 adjacent to the ring-shaped opening 118, such that there is a ring-shaped opening passing through the entire assembly. The front and rear panels 128 and 130 may also be attached to the drainage member around drainage opening 122. The case 102 may be attached to the drainage member 114 by adhesive, welding or heat sealing.

Referring to FIG. 12, the collapsible case 102 extends proximally from the drainage member 114 and surrounds the catheter tube 106. The collapsible case 102 also includes an opening 146 (FIGS. 8 and 9) in the proximal end 126 thereof. When the case 102 is collapsed, the catheter tube 106 passes through opening 146 to expose the catheter tube 106, as shown in FIG. 9. Referring to FIG. 12, the case 102 may include an insertion aid 148 therein and in association with opening 146. The insertion aid 148 includes an insertion tip 150 that is positioned in or extends from opening 146 of the case 102. The insertion tip 150 can be placed at the urethral opening to assist with the insertion of the catheter 104 into the urethra. The insertion aid 148 may also include distally extending arms or shoulders 152 which contact the inner walls of the case 102 and may be used as finger grips to collapse the case 102 during use. The one or more shoulders are ergonomically shaped, sized and spaced from the ring-shaped drainage member such that a user may have a finger located in the ring-shaped drainage member and one or more fingers engaged with the one or more shoulders.

During packaging and assembly, the drainage opening 122 of the drainage member 114 and the opening 146 in the proximal end 126 of the case 102 may be closed or sealed to seal the interior of the case 102 from the outer atmosphere. For example, referring to FIG. 11, the case 102 may include a removable seal, such a peelable adhesive strip 156, that covers the drainage opening 122 and the proximal opening 146. The removable seal may be one strip or two separate strips. Alternatively, the proximal opening 146 of the case 102 and/or the insertion aid 148 may include a breakable seal, such as a frangible heat or adhesive seal that breaks when the proximal end of the catheter is pushed through the opening.

The catheter 104 may be a gel-lubricated catheter or a hydrophilically coated catheter. When the catheter 104 is a gel-lubricated catheter, the case 102 may include a gel applicator (not shown) that dispenses gel onto the catheter tube 106 as the case 102 is collapsed. FIG. 13 illustrates one embodiment of an assembly wherein the catheter 104 includes a hydrophilic coating and the case 102 provides a vapor atmosphere for hydrating the hydrophilic coating. In this embodiment, front and rear panels 128 and 130 are made from a liquid and gas impermeable material. The case 102 also includes a compartment 158 that is formed from a liquid impermeable, vapor permeable material and holds a liquid, such as water, separated from the catheter. The liquid provides a vapor that permeates through the compartment 158 and creates a vapor hydrating atmosphere in the case 102 which hydrates the hydrophilic coating. In this embodiment, the compartment 158 has a serpentine configuration which includes interconnected generally elongated sub-compartments 160 connected by fluid passages 162. This serpentine configuration of the compartment 158 allows the compartment to easily collapse when the case 102 is collapsed. In another embodiment, the case 102 may include a liquid in direct contact with the hydrophilic coating to hydrate the hydrophilic coating.

Referring to FIG. 10, multiple catheter assemblies 100, 100a may be provided to the user in a recloseable pouch 164, so that the user may conveniently carry a supply of catheter assemblies. When the user is ready to perform catheterization, the user may open the reclosable pouch 164 and remove a catheter assembly 100. The user then removes the seal 156, shown in FIG. 11, when one is present. Referring to FIGS. 14 and 15, the user places a finger, such as an index finger or thumb, through the ring-shaped opening 118 of the drainage member 114 and other fingers against the proximal end 124 of the case 102 and presses on the arms of the insertion aid (not shown), when one is present. The user places the opening of the case, or the insertion tip when an insertion aid is present, against the opening of the urethra. The user then moves its fingers together to collapse the case 102 and insert the catheter tube 106 into the urethra to perform catheterization. The ability for the user to conveniently and easily manipulate the catheter and drainage member with a finger inserted in the ring-shaped opening of the drainage member and because the ring-shaped opening is located proximal of the drainage opening of the drainage member, the user is less likely to get urine on their hands during catheterization.

As can be seen from the above description, the present disclosure has several different aspects, which are not limited to the specific structures shown in the attached drawings and which do not necessarily need to be used together. Variations of these concepts or structures may be embodied in other structures without departing from the present invention.

What is claimed is:

1. A urinary catheter, comprising:
   a catheter tube having a proximal insertion end portion, a distal end portion and a lumen;
   a drainage member associated with the distal end portion of the catheter tube, the drainage member defining one or more generally ring-shaped openings configured to receive a finger of a user, and the drainage member having at least one arcuate drainage passageway extending along and following one side of the ring-shaped opening and said drainage passageway being in fluid communication with the lumen of the catheter tube; and
   a drainage opening in fluid communication with the at least one arcuate drainage passageway, wherein the drainage opening is co-axial with a longitudinal axis of the catheter tube.

2. The urinary catheter of claim 1, wherein the catheter tube has a hydrophilic coating thereon.

3. The urinary catheter of claim 1, wherein the one or more ring-shaped openings are shaped and sized for convenient grasping and manipulation of the urinary catheter during a catheterization procedure.

4. The urinary catheter of claim 1, wherein the at least one passageway comprises a second passageway that extends along the other side of the ring-shaped opening.

5. The urinary catheter of claim 1, wherein the drainage member includes a stem connected to the catheter tube.

6. The urinary catheter of claim 5, wherein the stem is bendable.

7. The urinary catheter of claim 6, wherein the stem extends at an angle from one or both of the drainage member or the distal end portion of the catheter tube.

8. The urinary catheter of claim 1, wherein the one or more ring-shaped openings comprise one ring-shaped opening.

9. An assembly, comprising:
   the urinary catheter of claim 1; and a case including a cavity, wherein at least the catheter tube is located in the cavity of the case.

10. The assembly of claim 9, wherein the case comprises a collapsible case surrounding at least the catheter tube.

11. The assembly of claim 10, in which the collapsible case has a proximal opening for passage of the catheter tube therethrough.

12. The assembly of claim 11, further including an introducer element associated with the proximal opening of the case.

13. The assembly of claim 10, wherein the collapsible case includes one or more shoulders at a proximal end of the case and wherein the one or more shoulders are configured for engagement with a user's fingers for collapsing the case.

14. The assembly of claim 13, wherein the one or more shoulders are sized and spaced from the drainage member such that a user may have a finger located in the one or more ring-shaped openings and one or more fingers engaged with the one or more shoulders.

15. The assembly of claim 11, wherein the proximal opening of the case includes an openable seal.

16. The assembly of claim 9, wherein the case comprises a hollow tube defining the cavity and having a closed proximal end and an opening at a distal end thereof.

17. The assembly of claim 16, wherein the drainage member extends from the opening at the distal end of the hollow tube.

* * * * *